(12) United States Patent
Moon et al.

(10) Patent No.: US 11,435,368 B2
(45) Date of Patent: Sep. 6, 2022

(54) BIOMARKER FOR SENESCENCE AND ANTI-SENESCENCE AND USE THEREOF

(71) Applicants: CHA University Industry-Academic Cooperation Foundation, Pocheon-si (KR); The General Hospital Corporation, Boston, MA (US)

(72) Inventors: Ji Sook Moon, Seoul (KR); Hak Ho Lee, Acton, MA (US); Ala Jo, Seoul (KR); Jae Hyun Park, Suwon-si (KR); Ji Min Park, Gwangju-si (KR); Chul Woo Lim, Seoul (KR); Yu Ri Choi, Seoul (KR)

(73) Assignees: CHA University Industry-Academic Cooperation Foundation, Pocheon-si (KR); The General Hospital Corporation, Boston, MA (US)

( * ) Notice: Subject to any disclaimer, the term of this patent is extended or adjusted under 35 U.S.C. 154(b) by 3 days.

(21) Appl. No.: 16/206,080

(22) Filed: Nov. 30, 2018

(65) Prior Publication Data
US 2020/0103422 A1    Apr. 2, 2020

(30) Foreign Application Priority Data
Sep. 27, 2018  (KR) .................. 10-2018-0115352

(51) Int. Cl.
*G01N 33/92*    (2006.01)

(52) U.S. Cl.
CPC .................... *G01N 33/92* (2013.01)

(58) Field of Classification Search
CPC ........... G01N 33/92; G01N 2800/7042; G01N 33/88; G01N 33/54326
See application file for complete search history.

(56) References Cited

U.S. PATENT DOCUMENTS

| | | | |
|---|---|---|---|
| 5,589,344 A * | 12/1996 | Contestable ..... | G01N 33/54306 435/7.9 |
| 8,624,002 B2 * | 1/2014 | Gu .................. | A61P 9/00 530/387.3 |
| 9,341,615 B2 | 5/2016 | Collino et al. | |
| 11,125,745 B2 * | 9/2021 | Lee .................. | G01N 27/28 |
| 2005/0009005 A1 * | 1/2005 | Watkins ........... | G01N 33/6893 435/4 |
| 2005/0027004 A1 * | 2/2005 | Kyle ................. | A61K 31/20 514/560 |
| 2007/0105104 A1 * | 5/2007 | Golz ................. | G01N 33/74 435/6.16 |
| 2011/0229883 A1 | 9/2011 | Spur et al. | |
| 2014/0162283 A1 * | 6/2014 | Riley ................. | G01N 33/5695 435/7.1 |
| 2015/0010673 A1 * | 1/2015 | Collino ............ | G01N 33/6893 426/2 |
| 2015/0152172 A1 * | 6/2015 | Wojciak ........... | A61K 47/62 424/172.1 |

FOREIGN PATENT DOCUMENTS

| | | | |
|---|---|---|---|
| JP | 2015-511020 A | 4/2015 | |
| WO | WO-2013117713 A1 * | 8/2013 | ......... C12N 15/1135 |

OTHER PUBLICATIONS

Pistolesi et al. (Neurochemical Research 1988 vol. 13, p. 817-821) (Year: 1988).*
Badawi et al. (Carcinogenesis 2004 vol. 25, p. 1681-1688). (Year: 2004).*
Brose et al. (J. Lipid Research 2011 vol. 52, p. 850-859). (Year: 2011).*
Qian et al. (J. Aging Research 2012 Article ID 121390, 16 pages) (Year: 2012).*
Aviva System Biology (Catalog Apr. 2016) (Year: 2016).*
Tokuda et al. (J. Oleo Science 2014 63:219-227) (Year: 2014).*
Combrinck et al. (J. Neuro. Neurosurg. Psychiatry 2006 77:85-88) (Year: 2006).*
Hartmann et al. (J. Alzheimer's Disease 2014 41:715-717) (Year: 2014).*
Dunn et al. (J. Alzheimers Dis. 2015 43:893-903 (Year: 2015).*
Amtul et al. Neurobiology of Aging 2012 33:831 (Year: 2012).*
Am. J. Clin. Nutr. 2012 95:420 (Year: 2012).*
Samieri et al. Am. J. Clin. Nutr. 2008 88:714 (Year: 2008).*
Taylor et al. Behav. Brain Res 2010 211:1 (Year: 2010).*
The Rotarod Assay in Alzheimer's Disease 2020 (total 9 pages) (Year: 2020).*
Jeong, S. et al. "Integrated Magneto-Electrochemical Sensor for Exosome Analysis," ACS Nano., 10(2), doi:10.1021/acsnano. 5b07584, 2016, pp. 16.
Undurti N. Das, "Ageing: Is there a Role for Arachidonic Acid and Other Bioactive Lipids? A Review", Journal of Advanced Research, (Feb. 2018), vol. 11, 2018, pp. 67-79.

* cited by examiner

*Primary Examiner* — Changhwa J Cheu
(74) *Attorney, Agent, or Firm* — Oblon, McClelland, Maier & Neustadt, L.L.P.

(57) ABSTRACT

Provided are a biomarker for diagnosing of the level of senescence, a composition and kit for diagnosing of the level of senescence to detect the biomarker, and a method of diagnosing the same. According to the composition and kit for the diagnosis of the level of senescence and the method of diagnosing senescence, the level of senescence of a subject is easily diagnosed, the health conditions of the subject are monitored, and a senescence-associated disease is prevented or diagnosed.

8 Claims, 8 Drawing Sheets

BIOMARKER FOR SENESCENCE AND ANTI-SENESCENCE AND USE THEREOF

CROSS-REFERENCE TO RELATED APPLICATION

This application claims the benefit of Korean Patent Application No. 10-2018-0115352, filed on Sep. 27, 2018, in the Korean Intellectual Property Office, the disclosure of which is incorporated herein in its entirety by reference.

BACKGROUND

1. Field

The present disclosure relates to a biomarker for the diagnosis of senescence and anti-senescence, a composition and kit for the diagnosis of the level of senescence and anti-senescence to detect the biomarker, and a method of diagnosing the level of senescence by using the same.

2. Description of the Related Art

Human bodies are always likely to maintain certain states. However, through 'senescence', homeostasis begins to break, where senescence means that each part of the human body is degenerated in such a way that it cannot survive the pathological conditions and states. As senescence progresses, the levels of proteins in bodies are decreased, energy metabolism is changed, and DNA is damaged. In other words, there is a change in the amount of hormones in bodies, the cellular senescence progresses, and the regenerative capacity of tissues is decreased, thus reducing the ability of the body to maintain homeostasis. Senescence is recognized as a major risk factor for various chronic diseases that reduce the quality of life and is pointed out as a social problem. However, senescence is a very complex phenomenon and is considered unpredictable due to the lack of reliable biomarker for senescence. Accordingly, when a senescence process representing the human body can be explained, it is expected to open a way to prevent senescence-associated diseases that develop due to senescence.

However, the current research into senescence is focused on specific tissues such as muscles and skin. Although lipofuscin and lipid peroxidation are known as biomarkers, there is still a need to develop a biomarker having high accuracy. That is, due to a technical limit in predicting senescence, there is a need to develop a diagnostic tool that can detect markers for senescence, anti-senescence, and diseases, and that quickly and easily measures markers, to prevent senescence-related diseases.

SUMMARY

Provided are biomarkers capable of diagnosing senescence and an anti-senescence level, a composition and a device for diagnosing of a senescence level including an agent for measuring the level of arachidonic acid (AA) metabolite, and a method of diagnosing a senescence level or senescence associated disease using the AA metabolite, and a method of screening for a material preventing or treating senescence associated disease.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
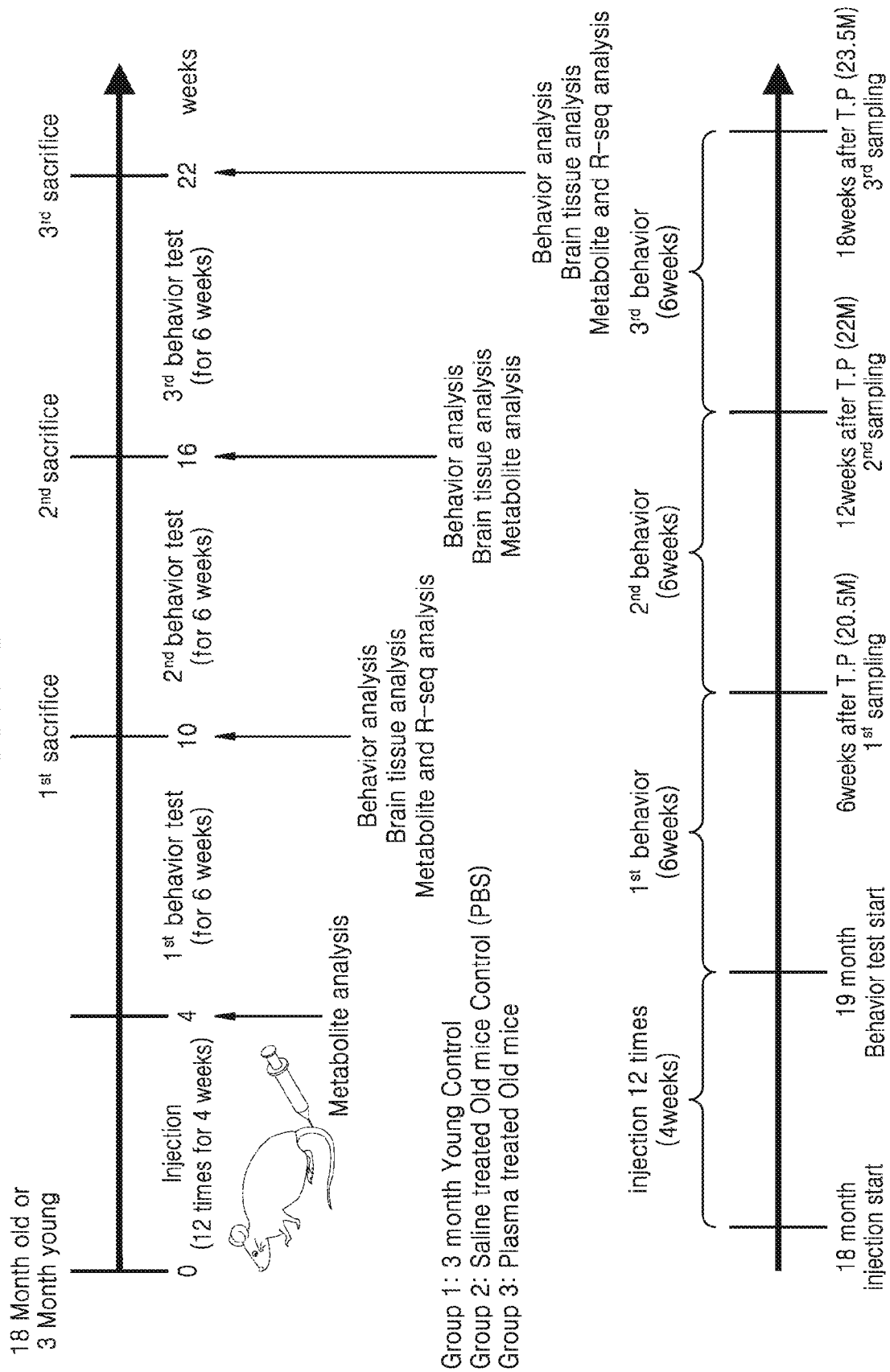
FIG. 1 illustrates the overall experimental scheme for screening senescence and anti-senescence associated biomarkers.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

One aspect provides a method of diagnosing a level of senescence of a subject, the method including: forming a complex by contacting a sample separated from the subject with one or more materials specifically binding to one or more arachidonic acid (AA) metabolites; measuring an expression level of one or more AA metabolites in the sample by measuring a level of the complex; comparing the measured expression level of the selected one or more AA metabolites in the sample with that of the same metabolite(s) in a control group; and in the case of changes in the expression level of the one or more AA metabolites in the sample as compared with the control group, determining whether the level of senescence of the subject is low or level of senescence of the subject is high.

The AA metabolite may be selected from metabolites shown in [Table 1] and may include functional equivalents thereof.

TABLE 1

| Metabolite name | Kegg ID | Metabolite name | Kegg ID |
|---|---|---|---|
| 5,6-Epoxy-8,11,14-eicosatrienoic acid | C14768 | Prostaglandin E2 | C00584 |
| 8,9-Epoxyeicosatrienoic acid | C14769 | Prostaglandin A2 | C05953 |
| 11,12-Epoxyeicosatrienoic acid | C14770 | Prostaglandin J2 | C05957 |
| 14,15-epoxy-5,8,11-eicosatrienoic acid | C14771 | Delta-12-Prostaglandin J2 | C05958 |
| Leukotriene E4 | C05952 | Prostaglandin I2 | C01312 |
| Arachidonic acid | C00219 | Thromboxane A2 | C02198 |
| 15H-11,12-EETA | C14781 | 16(R)-HETE | C14778 |
| 11H-14,15-EETA | C14813 | 8(S)-HPETE | C14823 |
| 15(S)-HPETE | C05966 | 12(R)-HPETE | C14812 |
| 12(S)-HPETE | C05965 | 20-Hydroxy-eicosatetraenoic acid | C14748 |
| 15(S)-HETE | C04742 | 11(R)-HPETE | C14820 |
| Hepoxilin B3 | C14810 | 15-KETE | C04577 |
| Hepoxilin A3 | C14808 | Lipoxin B4 | C06315 |
| 5(S)-Hydroperoxyeicosatetraenoic acid | C05356 | Lipoxin A4 | C06314 |
| Leukotriene A4 | C00909 | 19(S)-HETE | C14749 |
| Leukotriene B4 | C02165 | 5-HETE | C04805 |
| Prostaglandin H2 | C00427 | Phosphatidyl-choline | C00157 |
| Prostaglandin D2 | C00696 | 20-Hydroxy-leukotriene B4 | C04853 |
| 15-Keto-prostaglandin F2a | C05960 | | |
| Prostaglandin B2 | C05954 | | |
| 15-Deoxy-d-12,14-PGJ2 | C14717 | | |

The term "senescence" used herein refers to a change in characteristics over time. The senescence of a cell may include at least one selected from, compared to reference cells, reduction in cell proliferation ability, an increase in lipofuscin accumulation, an increase in the activity of β-galactosidase, an increase in mitochondrial reactive oxygen species, mitochondrial membrane potential reduction, and a decrease in the period of G0 and/or G1 period of cells, or a process causing these. Young cells may include at least one selected from, compared to reference cells, an increase in cell proliferation ability, a decrease in lipofuscin accumulation, a decrease in the activity of β-galactosidase, a decrease in mitochondrial reactive oxygen species, a mitochondrial membrane potential increase, and an increase in the period of G0 and/or G1 period of cells. For example, old cells refer to cells of which doubling time is at least two times, at least 3 times, at least 4 times, at least 5 times, at least 6 times, at least 7 times, at least 9 times, at least 10 times, at least 50 times, or at least 100 times the doubling time of passage number 2. In the case of humans, cells obtained from humans of the age of at least about 30 years old, the age of at least about 40 years old, the age of at least about 50 years old, the age of at least about 60 years old, the age of at least about 70 years old, the age of at least about 80 years old, the age of at least about 90 years old, and the age of at least about 100 years old are old cells.

The term "anti-senescence" used herein includes the delay or prevention of the senescence of a cell or a subject, or conversion of old cells into young cells.

The method may be provided for the diagnosis of the levels of senescence and anti-senescence. In this regard, the diagnosis of the levels of senescence and anti-senescence diagnosis may be the diagnosis of a senescence-associated disease or the providing of information about the levels of senescence and anti-senescence. The senescence-associated disease may be, for example, progeria, cognitive disorders (Alzheimer, Parkinson's disease, dementia, or a combination thereof), strokes, diabetes, arthritis, atherosclerosis, heart disease, hair loss, wrinkles, and osteoporosis. The information about the levels of senescence and anti-senescence may be information about biological ages. The term "biological age" is also referred to as the age of the living body, and refers to a time scale used when describing growth, maturation, or senescence. The age is represented as a scale of the calendar such as year, month, and day, that is, a chronological age. However, since growth, maturation, or senescence phenomena are not all the same, the concept of the biological age is introduced in addition to the chronological age. The anti-senescence efficacy of candidates for the anti-senescence may be confirmed by measuring the anti-senescence level.

The "diagnosis" may indicate determining the subject's susceptibility to a particular disease or condition, determining whether a subject has a particular disease or condition, determining or monitoring the prognosis of a subject that has a specific disease or condition, or evaluating or measuring the levels of senescence or anti-senescence.

The term "marker" or "biomarker" used herein refers to a material that is used to distinctively evaluate an old subject and a young subject, and may be an organic biomolecule such as a polypeptide, a nucleic acid (e.g., mRNA), a lipid, a glycolipid, a glycoprotein, a sugar (monosaccharide, a disaccharide, an oligosaccharide, etc.), which shows an increase or decrease in an amount thereof in the old subject compared to in the young subject. A marker for the diagnosis of senescence or anti-senescence of a subject according to an aspect may be an AA metabolite of which expression is decreased in an old subject compared to a young subject.

The term "metabolite" used herein refers to a metabolite derived from a sample of biological origin, such as whole blood, plasma, serum, or platelet. In one embodiment, the sample of biological origin may be plasma. The metabolite may include a substance produced by metabolic processes, or a substance produced by chemical metabolism by biological enzymes and molecules, or the like. The term "biological sample" used herein may be a sample isolated from a subject who has senescence-associated disease or who is susceptible to senescence-associated disease, or a cultured cell. The biological sample may be blood, plasma, serum, tissue, urine, mucus, saliva, tears, sputum, spinal fluid, pleural fluid, nipple suction, lymphatic fluid, airway fluid, serous fluid, urogenital fluid, breast milk, lymphatic fluids, semen, cerebrospinal fluid, body fluid in system, ascites, cystic tumor body fluids, saline fluids, tissues, or combinations thereof, a cystic tumor body fluid, a saline fluid, a tissue, or a combination thereof. When the biological sample is blood or plasma, since blood or plasma, which is easy to collect, is used as a sample, the analysis may be easily carried out without incurring a burden of extracting an organ in a subject. The cell may be a cell isolated from the subject or a cultured cell.

The term "arachidonic acid (AA)" used herein refers to an omega-6 fatty acid and is involved in some biological processes such as the development of muscle and brain and inflammatory responses. The relationship between levels of AA and metabolite thereof circulating in the body and senescence is not known. The term "measurement of levels" refers to a process of identifying the levels of AA metabolite in a biological sample for the diagnosis of the senescence level. According to an embodiment, the levels of metabolite shown in [Table 1] may be identified. Analytical methods for this purpose include, but are not limited to, mass spectrometry, chromatography, nuclear magnetic resonance, or an integrated magneto-electrochemical sensor (iMES) assay. The chromatography may be liquid chromatography (LC), liquid-solid chromatography (LSC), paper chromatography (PC), thin-layer chromatography (TLC), gas-solid chromatography (GSC), liquid-liquid chromatography (LLC), formal chromatography (FC), emulsion chromatography (EC), gas-liquid chromatography (GLC), ion chromatography (IC), gel filtration chromatography (GFC), or gel permeation chromatography (GPC). In one embodiment, the chromatography may be liquid chromatography or ultra performance liquid chromatography (UPLC). However, the chromatography is not limited thereto.

One or more materials specifically binding to one or more AA metabolites, or an agent for the measurement of the levels of metabolite refers to an agent that is used to quantitatively detect the AA metabolite from a biological sample isolated from a subject. The agent is not limited, and when a target component is an amino acid, the agent may be a primer, a probe, a nucleotide, an antibody or an antigen-binding fragment thereof, a ligand, a receptor, an agonist or an antagonist, a protein, or any combination thereof, each of which binds to one or more metabolites selected from metabolites shown in Table 1.

The one or more materials specifically binding to one or more AA metabolites may be bound to magnetic beads. The magnetic beads are labeled with one or more enzymes.

Measuring of the expression level may be performed by detecting from the one or more enzymes. The enzymes may be selected from horse radish peroxidase (HRP), alkaline phosphatase (ALP), β-D-galactosidase (β-Gal), or any combination thereof. The signals are electrical currents released from the enzyme.

The term "antibody" as a term known in the art may refer to a specialized immunoglobulin which is directed toward an antigenic site. The antibody may specifically bind to the metabolites shown in [Table 1].

The antibody may be in the form of a polyclonal antibody, a monoclonal antibody, or a recombinant antibody, and in this regard, all the immunoglobulin antibodies fall within the range of the antibody of the present inventive concept. The antibody may be in a complete form composed of two full-length light chains and two full-length heavy chains. In addition, the antibody may be a special antibody, such as a humanized antibody. The polyclonal antibody may be prepared according to a conventional method known in the art by injecting an immunogen (e.g., a biomarker protein or a fragment thereof) into a foreign host. The foreign host may include a mammal, such as a mouse, a rat, a sheep, and a rabbit. When the immunogen is injected in an intramuscular, intraperitoneal, or subcutaneous manner, it can be administered with an adjuvant to generally increase antigenicity. Then, blood may be regularly collected from the foreign host to collect serum showing improved titer and specificity for an antigen, or to separate and purify antibodies therefrom.

The monoclonal antibody may be prepared by cell line generation techniques by fusion known to those of skill in the art. For a brief description of a method of preparing the monoclonal antibody, Balb/C mice may be immunized with a suitable amount (e.g., 10 μg) of the protein that has been purified, or polypeptide fragments of the protein may be synthesized and combined with bovine serum albumin to immunize mice, and then, antigen-producing lymphocytes isolated from the mice may be fused with human or mouse myeloma to produce immortalized hybridoma cells. Then, according to ELISA, only hybridoma cells producing desired monoclonal antibodies are selected and cultured, and monoclonal antibodies may be separated and purified from the culture. In addition, the monoclonal antibody may be a commercially available antibody for the AA metabolites.

Such antibodies may be used to identify the protein expression in the biological sample according to suitable methods known in the art, such as ELISA, RIA, sandwich assay, or western blotting or immunoblotting on a polyacrylamide gel.

Another aspect provides a method of diagnosing senescence-associated disease of a subject, the method including: forming a complex by contacting a sample separated from the subject with one or more materials specifically binding to one or more arachidonic acid (AA) metabolites selected from metabolites shown in Table 1; measuring an expression level of one or more AA metabolites selected from the Table 1 in the sample by measuring a level of the complex; comparing the measured expression level of the selected one or more metabolites in the sample with that of the same metabolite(s) in a control group; and in the case of changes in the expression level of the one or more metabolites in the sample as compared with the control group, determining whether the subject has senescence-associated disease or a high risk of occurrence of senescence-associated disease.

Another aspect provides a method of screening a material preventing or treating senescence associated disease, the method including: administering a candidate material to a subject; separating a sample from the subject; forming a complex by contacting the separated sample with a material specifically binding to one or more arachidonic acid (AA) metabolites selected from metabolites shown in Table 1; measuring an expression level of the metabolites in the sample by measuring a level of the complex; comparing the measured expression level of the metabolites in the sample with that of the same metabolites in a control group; and, in the case of changes in the expression level of the metabolites in the sample as compared with the control group, determining whether the candidate material is efficient in preventing or treating senescence associated disease.

Another aspect provides a device for diagnosing a level of senescence of a subject, the method including: a recognition surface including an immobilized biomolecule, wherein the immobilized biomolecule is a material capable of specifically binding to one or more arachidonic acid (AA) metabolites selected from metabolites shown in Table 1 from a sample; and A sensor surface including a plurality of electrodes configured to detect the metabolites, Wherein the recognition surface and the sensor surface are arranged spaced apart from each other facing each other.

The device may further include a sample required for the diagnosis of the level of senescence.

In one embodiment, the device may be an integrated magneto-electrochemical sensor kit, but is not limited thereto. An integrated magneto-electrochemical sensor refers to a system for detecting electrical signals by enzymatic signal amplification by using magnetic beads. In detail, the integrated magneto-electrochemical sensor refers to a system in which a substance (for example, an antibody) capable of detecting a target substance is attached on the magnetic beads, and electrical signals by enzymatic signal amplification generated by using chromogenic material (for example, horse radish peroxidase (HRP), alkaline phosphatase (ALP), β-D-galactosidase (β-Gal)), capable of detecting the target material, are detected. The kit is a modification of iMES of Lee et al. (Integrated Magneto-Electrochemical Sensor for Exosome Analysis, ACS Nano.

2016 Feb. 23; 10(2): 1802-1809), and details thereof may be understood by referring to this paper. The modified iMES device has the following usages: i) Plasma or blood sample is used directly without purification. ii) The assay has high detection sensitivity through concentration and enzymatic signal amplification. iii) Based on electrical sensing methods, the kit may be manufactured as small portable devices.

The device may include a preparation, a kit, and a computer with an algorithm, each for measuring the AA metabolite level and may associate the measurements of the level of the marker with the senescence through the algorithm.

The subject may be a mammal. The mammal may be, for example, a human, a dog, a cat, a goat, a pig, a mouse, a rabbit, a hamster, a rat, or a guinea pig.

The senescence-associated disease may be selected from progeria, cognitive disorders, stroke, diabetes, arthritis, arteriosclerosis, heart disease, hair loss, wrinkles, and osteoporosis.

The cognitive disorder may be, but is not limited to, Alzheimer's disease, Parkinson's disease, dementia, or a combination thereof.

The measuring of the metabolite level may be performed by methods known to those skilled in the art. In one embodiment, the measuring process may be performed by using an integrated magneto-electrochemical sensor, but other methods may instead be used to perform the measuring process.

To provide information about the diagnosis of the levels of senescence and anti-senescence, clinical information other than the marker of the subject may be additionally used in addition to the marker analysis result. Such clinical information includes, for example, the age, sex, body weight, eating habit, body mass, ultrasound, computed tomography (CT), magnetic resonance imaging (MRI), and angiography of the patient.

When the level of AA metabolite is increased compared to a control, the method may further include determining that the level of senescence has been reduced. In one embodiment, when the level of AA metabolite is increased compared to a control, the method may further include determining that the level of anti-senescence has been increased. The term "the increase in the level of metabolite" used herein refers to a significant increase, which is measurable, in the concentration of metabolite in a sample of a subject compared to a control. For example, the metabolite is increased at least about 1.1 times, for example, from at least 1.1 times to at least 10 times, at least 1.1 times, at least 1.5 times, at least 2 times, at least 3 times, at least 4 times, at least 5 times, at least 6 times, at least 7 times, at least 8 times, at least 9 times, or at least 10 times.

When the level of AA metabolite is decreased compared to a control, the method may further include determining that the level of senescence has been increased. In one embodiment, when the level of AA metabolite is decreased compared to a control, the method may further include determining that the level of anti-senescence has been decreased. The term "the decrease in the level of metabolite" used herein refers to a significant decrease, which is measurable, in the concentration of metabolite in a sample of a subject compared to a control. For example, the metabolite is decreased at least about 0.9 times, for example, from at least 0.1 times to at least 0.9 times, at least 0.9 times, at least 0.8 times, at least 0.7 times, at least 0.6 times, at least 0.5 times, at least 0.4 times, at least 0.3 times, at least 0.2 times, or at least 0.1 times.

The control refers to a subject or cell of which senescence has not occurred or has less occurred, or a sample isolated from a subject or cell that has not had senescence-associated disease or is not likely to have senescence-associated disease.

Another aspect provides a method of screening a senescence inhibitor, the method including: incubating a cell and a test compound; measuring the level of AA shown in Table 1 in a biological sample isolated from the cell; and determining the test compound as a senescence inhibitor when the level of the measured AA metabolite is greater than the level of the control.

The term "senescence inhibitor" used herein refers to an anti-senescence agent, and may be a material that reduces the level of senescence.

The cell may be a cell isolated from the subject or a cultured cell. The cell may be, for example, a nerve cell, an immune cell, an epithelial cell, a reproductive cell, a muscle cell, or a cancer cell. The cell may be a cell line or a primary cultured cell.

The test compound may include a chemical substance, a protein, a nucleic acid, a lipid, or a combination thereof.

The incubation may be performed in in-vitro.

The control may be a negative control. The negative control may be a cell that is not incubated with the test compound.

According to a biomarker for the diagnosis of senescence and/or anti-senescence according to an embodiment, a composition and kit for the diagnosis of the level of senescence to detect the biomarker according to an embodiment, a method of diagnosing the level of senescence of a cell or a subject according to an embodiment, and a method of screening a senescence inhibitor according to an embodiment, the level of senescence may be measurable with high levels of accuracy and sensitivity. In addition, the level of senescence of a subject may be determined to provide information about the health condition of the subject and to screen a senescence inhibitor.

Hereinafter, embodiments will be described in more detail with reference to Examples. However, Examples are intended to illustrate one or more embodiments and the scope of the present disclosure is not limited to these Examples.

Example 1. Screening of Senescence and Anti-Senescence Related Biomarker

The design for an experiment to screen a senescence and anti-senescence related biomarker is illustrated in FIG. 1. Mice were treated with substances (stem cell, umbilical cord blood, a therapeutic agent for the treatment of senescence, an anti-senescence agent, or the like) known to be effective in regenerating or treating senescence or injury to identify senescence-associated biomarkers. In one embodiment, for such substances, umbilical cord blood, which is known to secrete factors that are effective for restoring senescence and injuries, was used. Metabolite assay was performed while performing behavioral tests on an old mouse administered with umbilical cord blood, old mice administered with saline, and a young mouse. Then, assayed metabolites were used as raw data for selecting senescence and anti-senescence associated biomarker candidates.

1.1. Experimental Animals and Treatment

Mice were raised at room temperature in a standard 12-hour light-dark cycle. All animal experiments were performed by animal experiments approved by the Animal Care and Use Committee (IACUC) of the University of CHA.

Human umbilical cord blood to be administered to mice was collected at the CHA General Hospital. Donated umbilical cord blood lacked clinical values because it had no mononuclear cells. Therefore, umbilical cord blood was donated in preclinical studies (IRB No. CHAMC-2015-08-130-009). The umbilical cord blood was centrifuged at 3,000 g for 15 minutes to obtain plasma, and used together with adenine (CPDA-1) as an anticoagulant and citrate-phosphate-dextrose (CPD). The isolated umbilical cord blood was stored at a temperature of −80 □ before use. The human umbilical cord blood prepared as described above or saline (130 μl) were intravenously injected 12 times into 18-month female C57BL/6 mice for 4 weeks. In this regard, 3-month young mice were used as a positive control, and experimental groups were as follows: Group 1, 3-month young mice (n=30); Group 2, 18-month old mice treated with saline (old mice non-treated, n=57); and Group 3, 18-month old mice treated with umbilical cord blood (old mice treated, n=30). After 4 weeks of the treatment with umbilical cord blood or saline, samples were collected for analysis of metabolites.

1.2. Behavioral Experiment

Figure 2:
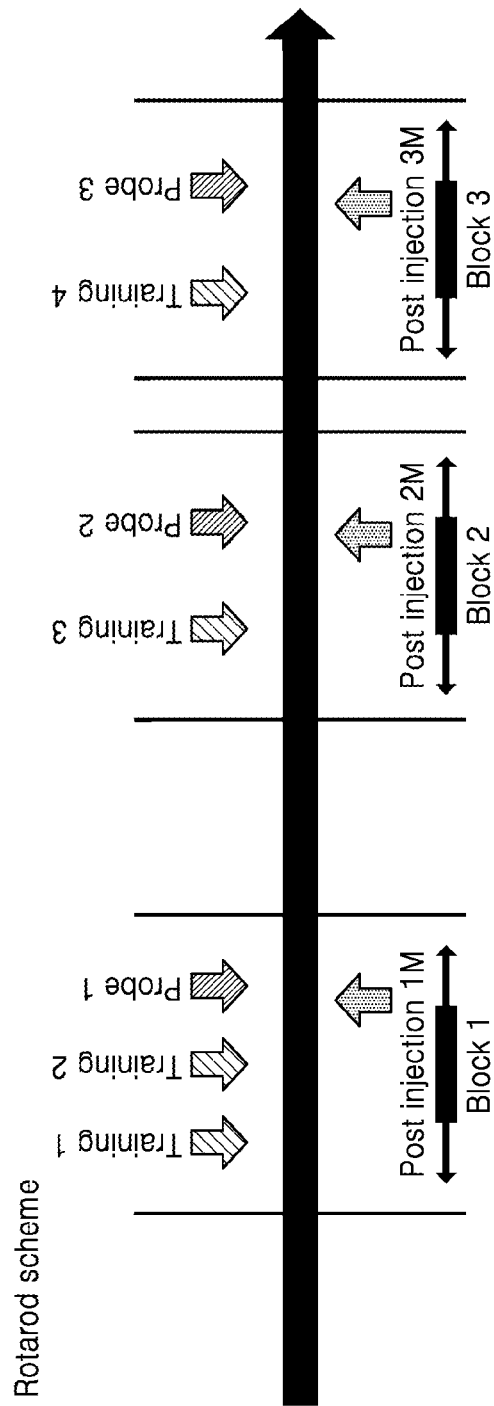
FIG. 2 illustrates a rotarod test for evaluating a long-term motor memory.

Each of the three experimental groups was subjected to a behavioral test three times for 6 weeks in total, and samples were collected. Specifically, to evaluate long-term exercise memory, a total third-order rotarod test was performed as shown in FIG. 2. A 3 cm-diameter rotor rod was accelerated at 4 rpm for 30 seconds for 5 minutes, starting at 4 rpm. The test was carried out three times a day for each mouse. In the primary rotarod test, the mice were trained for 3 days on a rotarod. The mice were retrained at the rotarod for the following two days. All the blood of the mice was collected by cardiac puncture to predict the metabolic change. In the secondary rotarod test, the mice were trained once for 3 days on the rotarod. Then, the blood of the mice was collected. In the tertiary rotarod test, the mice were trained once for 3 days on the rotarod. Then, the blood of the mice was collected. Each of the mice received a total of two test sessions including the first session of the 21st month and the second session of the 23rd month. In the first session, mice were trained on the rotaract for three days. In the second session, the mice were trained on the rotarod for two days. To predict metabolic change, the blood of mice was collected at the 21st month and the 23rd month. The collected blood was then used for metabolite analysis.

1.3. Selection of Senescence-Associated Biomarkers Through Statistical Analysis of Metabolites in Samples A liquid chromatography mass spectrometer (LC-MS) system of Agilent was used to perform a metabolite assay on blood samples collected above. LC-MS raw data was converted into mzXML format, which is an MS data standard data format, by ProteoWizard software [23051804]. Next, for data processing, data in the form of mzXML was used, by using an R package called as metabolite automatic identification toolkit (MAIT) [24642061]), to perform the extraction of m/z (the mass-versus-charge of the ionized metabolite) and retention time (time to stay in chromatography), statistical analysis and metabolism identification [24642061]. For subsequent analysis, the ionized metabolites were subjected to an analysis of variance (ANOVA) to match the known metabolites candidates based on molecular mass information with ionized metabolites with significant changes according to treatment or age. Principal component analysis (PCA) was performed to understand the unique structure of the metabolic data with thousands of features, and the principal components (PCs) were reduced to two having two largest variants. T-distributed stochastic neighbor embedding (t-SNE) analysis was performed by using the same ionized metabolite information used in the PCA through a Scikit-learn (python package) program to visualize the separation of groups. As functional analysis, metabolic pathways, in which metabolites with significant changes due to senescence and plasma treatment were stochastically gathered, were determined by KEGG pathway analysis of MetaboAnalyst 3.0, which is a web-based application [25897128].

Figure 3A:
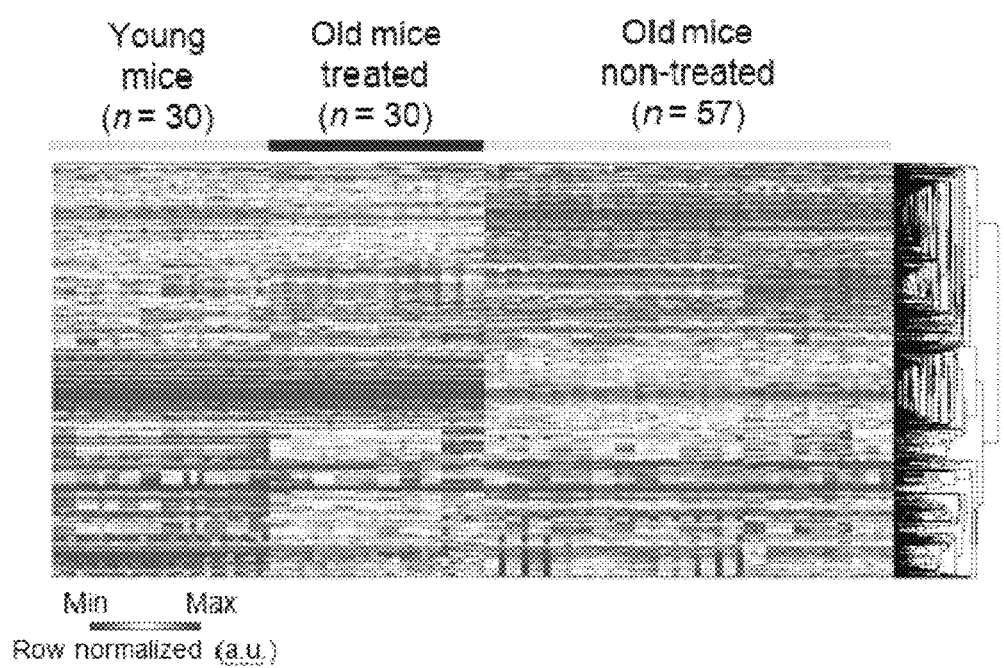
FIG. 3A illustrates results of a metabolic profiles obtained from a blood sample collected from mice subjected to a rotaract test mouse; Rows are hierarchically clustered (m/z value, retention time) from liquid chromatography and mass spectrometry (LC/MS) analyses and columns to samples.

FIG. 3A shows results of metabolic assay profiling obtained from a blood sample collected from the three experimental groups. Row: Characteristics (m/z value, delay time) obtained from LC/MS, column: sample. Relatively high expressions are illustrated in red, and relatively low expressions are illustrated in blue. The sample (column) was analyzed by setting the number of clusters to 3 by using K-Means cluster analysis.

Figure 3B:
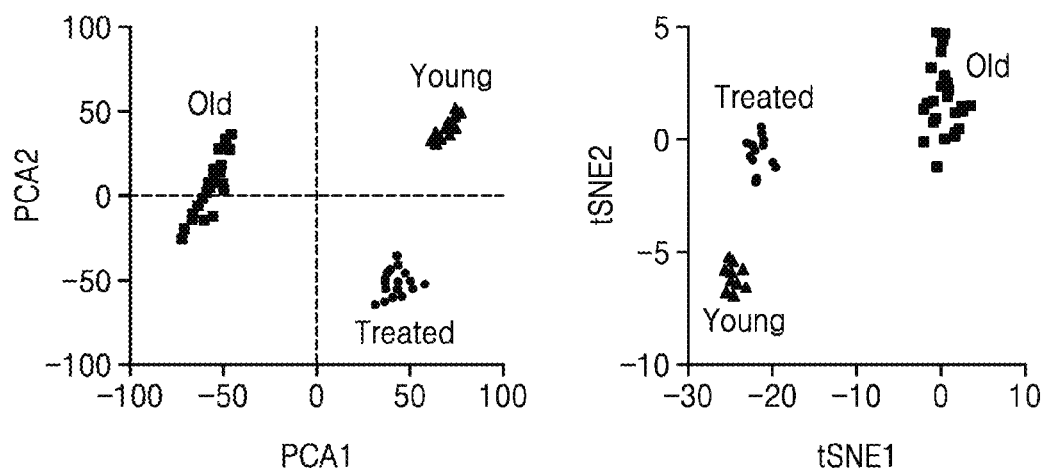
FIG. 3B illustrates a scree plot of principal component analysis (PCA) showing the variance of the 10 principal components, and a graph that efficiently visualizes clustering separation by performing t-SNE on the same ionized metabolite information as used in PCA.

FIG. 3B shows a scree plot of principal component analysis (PCA) showing the variance of the 10 principal components, and a graph that efficiently visualizes clustering separation by performing t-SNE on information about the same ionized metabolite as used in PCA. Principal components 1 and 2 represent about 50% of the total dispersion of the degree of production of ionized metabolites. PCA1 represents the cell treatment effect well. PCA2 represents the difference in age.

Figure 3C:
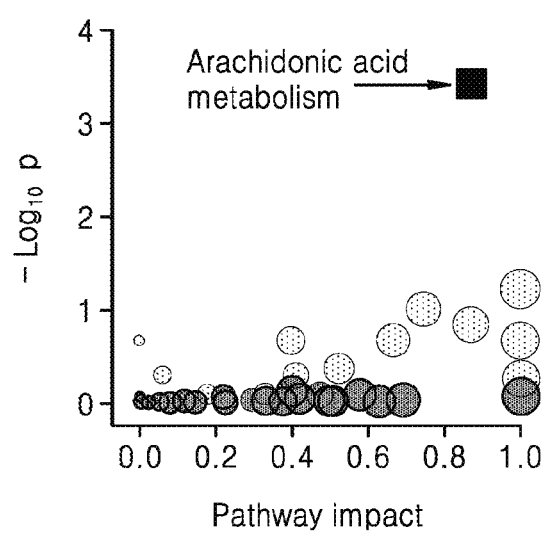
FIG. 3C illustrates a score plot of the PCA for dimensional reduction.

FIG. 3C shows a score plot of the PCA for dimensional reduction. The locations of the samples were visualized on two dimensions with respect to principal components (PC) 1 and 2. The value in parentheses in the axis legend is the dispersion ratio of a corresponding component. According to the variation of the three principal components, samples are classified. Samples tend to be classified in the same group.

The results indicate that the change in metabolite is affected by age and plasma treatment, which is confirmed based on metabolite profiling using hierarchical cluster analysis. As a result of the reduction of several features to two components by PCA analysis, approximately 50% of the total mutations showed that the plasma-treated young group (right in the scatter plot) and the older group (left) in two distinct locations. In the dispersion plot of PC scores, the plasma-treated older groups appeared to migrate into the younger group. This result shows an anti-senescence effect of plasma stem cells. The separation of the groups was more pronounced in the t-SNE analysis. Thus, a selected feature may be deduced as a metabolite biomarker associated with senescence and anti-senescence. As a result of the KEGG pathway analysis, the selected feature was identified as a metabolite associated with AA metabolism, so the AA metabolite was derived as a biomarker for diagnosis of the level of senescence.

Based on the above results, it was confirmed that 39 metabolites associated with AA metabolism shown in Table 1 were biomarkers for senescence and anti-senescence.

Experimental Example 1. Verification of the Level of Senescence Diagnostic Effect of AA Metabolite To verify the effects of AA metabolites on the levels of senescence and anti-senescence, the relationship between metabolite changes and behavioral phenotypes confirmed by a rotarod experiment was analyzed. Experiments were performed as in Example 1.2, and the running time of each mouse on the spinning rod was recorded.

Figure 4:
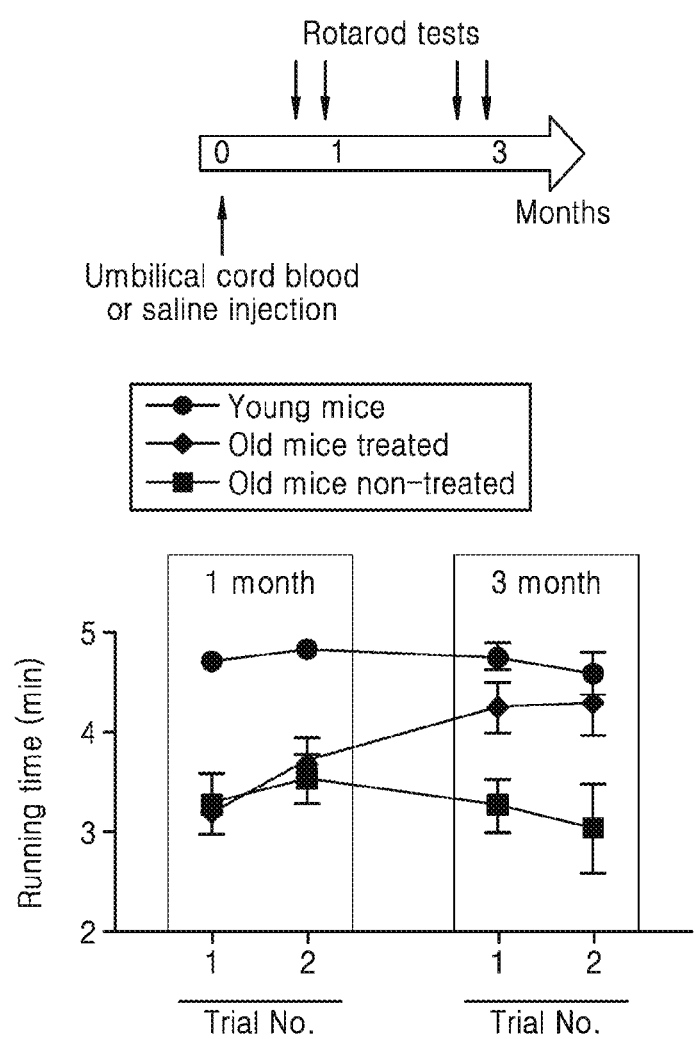
FIG. 4 illustrates a graph of the timing and the results of the 3-month period of a rotarod experiment with respect to the running time (min) after umbilical cord blood or saline was administered to young mice, 18-month old mice treated with saline (old mice non-treated), and old mice treated with umbilical cord blood (old mice treated)

FIG. 4 shows a graph of the timing and the results of the 3-month rotarod experiment with respect to the running time (min) after umbilical cord blood or saline was administered to young mice, 18-month old mice treated with saline (old mice non-treated), and old mice treated with umbilical cord blood (old mice treated).

As shown in FIG. 4, at the beginning of the experiment, the young mice had a significantly longer running time than the old mice. However, 3 months after the administration of umbilical cord blood, the running time of the umbilical cord blood-treated old mice was restored to a level similar to that of the young mice, while the running time of saline-treated senescence mice decreased over time.

Due to the treatment of old mouse with umbilical cord blood, the level of senescence of the mice was reduced and the long-term motor ability was restored. Accordingly, metabolites for the diagnosis of the level of senescence, derived from samples of the old mice, of which motor ability was restored, the old mice treated with saline, and the young mice are effective for the diagnosis of the level of senescence.

Example 2. Production of Biosensor for Detection of AA iMES was used to effectively detect AA in a blood sample. iMES combines the target enhancement and the target detection into a single platform. That is, target molecules are captured and labeled by using magnetic beads (MB), and target molecules bound to the beads are detected by electrochemical sensing. This approach has the following characteristics: i) natural samples (plasma or blood) may be used immediately without purification thereof; ii) the assay has high detection sensitivity through magnetic improvement and enzymatic signal amplification; iii) based on the electrical detection scheme, the sensor may be easily miniaturized as a portable device.

Figure 5:
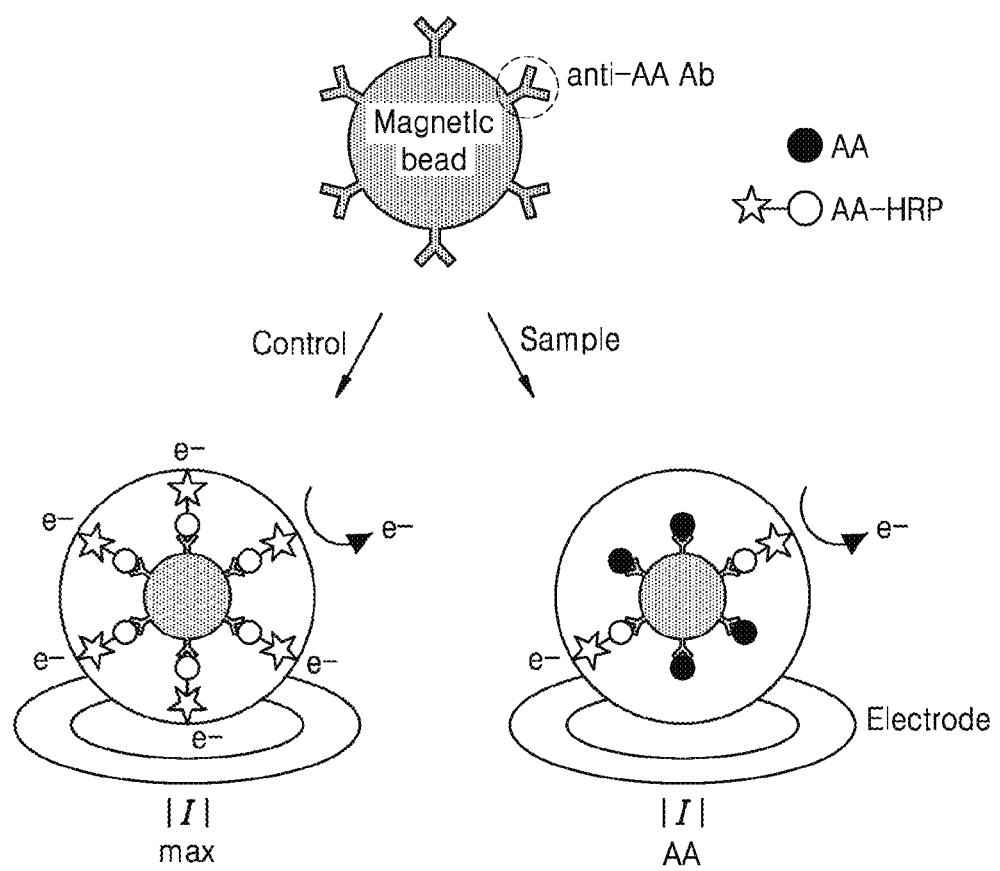
FIG. 5 illustrates a schematic diagram of iMES according to an aspect.

FIG. 5 shows a schematic diagram of iMES according to an aspect. It was difficult to find a pair of conjugates in the small molecule AA (304.4669 Da). Accordingly, a single antibody to AA was used. MB-AA was prepared by coating the magnetic beads (MB) with AA-antibodies to capture the target molecule AA. As a competitor thereof, AA conjugated with HRP (AA-HRP), which is an oxidase enzyme, was prepared. Analysis was initiated by mixing MB-AA with AA-HRP and plasma samples. Herein, the beads were bound to AA-HRP in inverse proportion to the amount of AA present in the plasma sample. Finally, the beads were mixed with a coloring electron carrier (3,3', 5,5'-tetramethylbenzidine: TMB) and loaded onto an electrode. The redox reaction of TMB by the electrode generates a current as a read signal. The current is competitively reduced due to the presence of AA in the sample. That is, the more the AA is present in the sample, the smaller the detected current signal. The production method will be described in detail below.

2.1. Preparation of Immune Magnetic Beads 5 mg of magnetic beads coated with epoxy (Dynabeads M-270 Epoxy, Invitrogen) was suspended in 100 µl of a 0.1 M sodium phosphate solution. 100 µg of antibody to AA (Biomatik) was added thereto and mixed thoroughly. 100 µl of a 3 M ammonium sulfate solution was added thereto and the mixture was incubated at room temperature for 2 hours and then overnight at 4 □ with slow tilt rotation. The magnetic beads were separated by a permanent magnet, washed twice with a PBS solution, and resuspended in 200 µl of PBS containing 1% BSA.

2.2. HRP Conjugation to AA

100 µg of BSA-conjugated AA (Biomatik) was dissolved in 0.5 ml of a 0.2 M carbonate-biocarbonate buffer solution (pH 9.4), and then the resultant solution was added directly to 1 mg of lyophilized EZ-link Plus Peroxidase (Thermo Scientific). The reaction product was incubated at room temperature for 1 hour. After 1 hour, 10 µl of sodium cyanoborohydride (Thermo Scientific) was added thereto and reacted at room temperature for 15 minutes. 20 µl of quenching buffer (Thermo Scientific) was added thereto and reacted at room temperature for 15 minutes. Finally, the HRP-conjugated AA was concentrated by using an Amicon Ultra 100K filter (Millipore).

2.3. Detection of Mouse Plasma AA

Mouse plasma samples (0.5 µl) were diluted with PBS containing 1% BSA and mixed with 50 µl of an immune magnetic bead solution (50 µl) and an HRP-conjugated AA solution. The mixture was incubated at room temperature for 1 hour while performing slow-tilt rotation. Control beads were prepared by mixing 50 µl of an immune magnetic bead solution, 50 µl of an HRP-conjugated AA solution, and 1% BSA in PBS (50 µl). The magnetic beads were separated by permanent magnets and washed twice with 80 µl of PBS (1% BSA). Finally, the beads were resuspended in 7 µl of PBS. The prepared bead solution and 20 µl of a TMB solution (Biomatik) were placed on an electrode. After 6 minutes, a chronoamperometry measurement was initiated with an electrochemical sensor. The current levels in the range of 40 to 45 seconds were averaged.

Experimental Example 2. Verification of the AA Detection Ability of the Biosensor of Example 2

Figure 6:
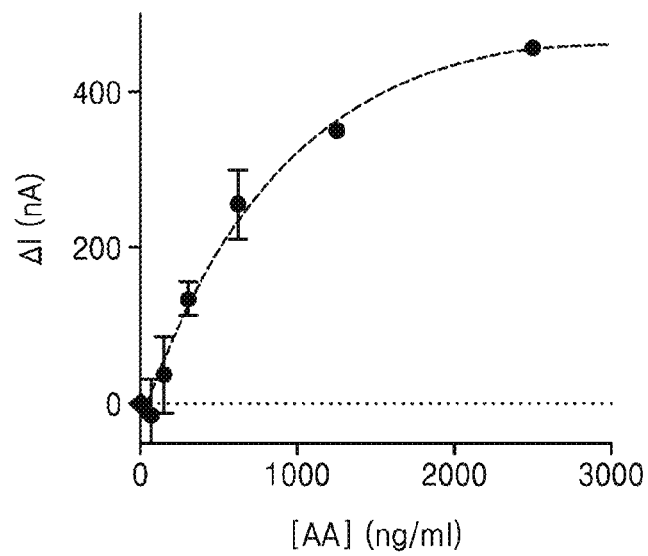
FIG. 6 illustrates a graph of the difference ($\Delta I$) in the current measured according to the arachidonic acid (AA) concentration in the experimental group mixed with AA-HRP.

In order to verify the ability of the biosensor of Example 2 to detect the change of AA in plasma, a control cultured with AA-HRP alone was prepared as a control and a plasma sample was prepared as an experimental group. As described in Example 2, the current of the sample was measured by using the iMES method and the current difference $I=I_{control}-I_{plasma}$ was calculated. FIG. 6 shows a graph of the difference ($\Delta$ I) in the current measured according to the AA concentration in the experimental group mixed with AA-HRP;

As shown in FIG. 6, the difference ($\Delta$I) of the measured current increases as the amount of AA in the experimental group increases, and the detection limit of the sensor is about 125.9 ng/ml. This detection limit is 250 times greater than the normal concentration of AA present in the plasma of young rats. By this method, the amount of plasma sample required for measurement could be optimized to 0.5 µl.

In addition, ELISA analysis was performed in parallel to compare the detection effects of AA in the above method to the ELISA method of the related art. In detail, an ELISA experiment was performed by using a mouse AA (AA) ELISA kit (Biomatik) according to the manufacturing guidelines. Samples were prepared by diluting AA samples with a fixed concentration. Some samples were quantified with iMES and some samples with ELSIA. When quantified by ELSIA, diluted AA was added to each well and incubated with AA-HRP for 40 min at 37° C. After washing, a TMB solution was added and incubation was performed for 20 minutes. A stop solution was added thereto to stop color development. Absorbance was read at the wavelength of 450 nm by using a microplate reader (Tecan). When the samples were quantified with iMES, the method described above was used.

Figure 7:
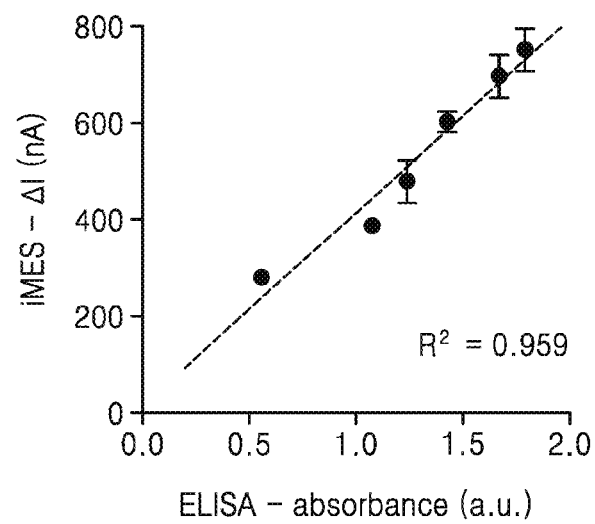
FIG. 7 illustrates a graph of AA measurements obtained from ELSIA and iMES methods.

FIG. 7 shows a graph of AA measurements obtained by using ELSIA and iMES methods with respect to a sample.

As shown in FIG. 7, there was a strong linear relationship ($R2=0.959$) between iMES results and ELISA results. Since the iMES analysis takes less time to analyze than the ELSIA analysis, it was confirmed that the iMES analysis provides excellent efficiency of detecting AA in the blood of the subject.

Experimental Example 3. The Level of Senescence Analysis in the Mouse by Using the Biosensor of Example 2

In Experimental Example 2, it was confirmed that the iMES method was effective for detecting AA in the blood, and the AA level was analyzed in the blood samples of the old mice and the young mice by the iMES method.

Figure 8:
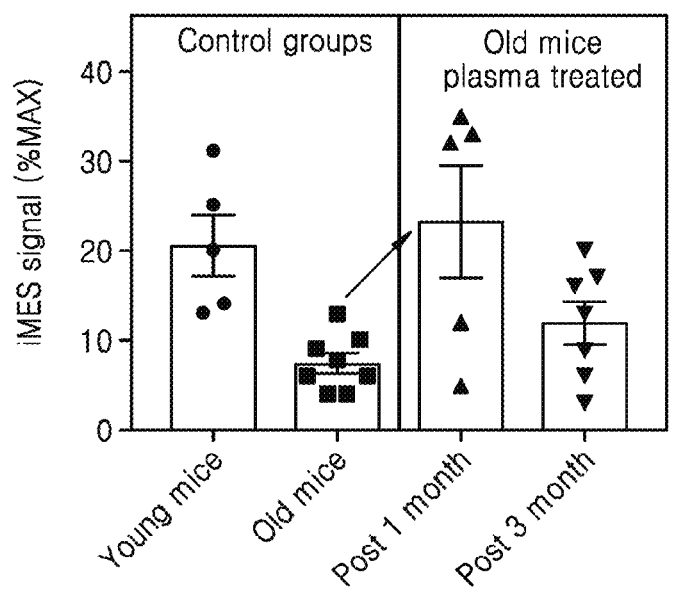
FIG. 8 illustrates measurements of AA levels obtained from a biosensor according to an aspect in blood samples of young mice (less than 8 months, n=65) and old mice (20 and 23 months, n=28)

FIG. 8 shows measurements of AA levels obtained by using a biosensor according to an aspect in blood samples of young mice (less than 8 months, n=65) and old mice (20 and 23 months, n=28).

Figure 9:
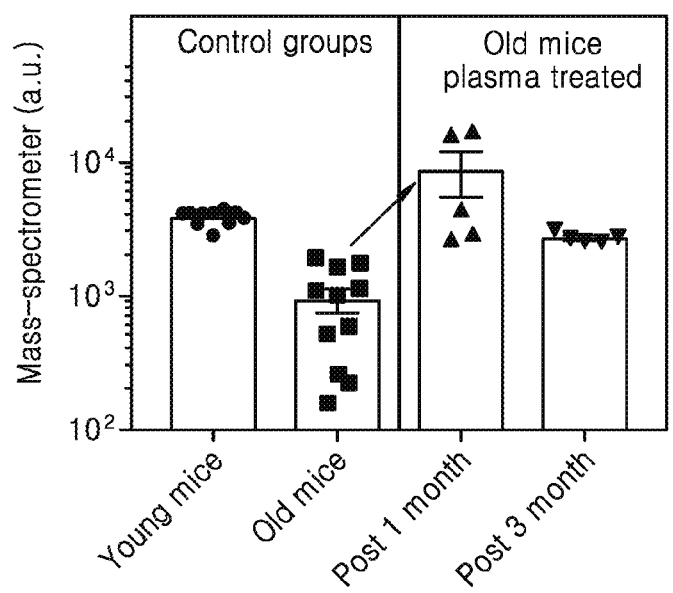
FIG. 9 illustrates the AA levels measured by mass-spectrometer in blood samples of young mice (less than 8 months, n=65) and old mice (20 and 23 months, n=28).

As shown in FIG. 8, it was confirmed that the concentration of AA was increased in the blood of old mice after treatment with umbilical cord blood, and this result was consistent with the result of the measurement of the mass-spectroscopy intensity (FIG. 9).

As described above, the level of AA in the blood was able to be efficiently detected by using the method of Example 2.

From the above results, it was confirmed that the level of senescence of a mouse is effectively diagnosed by identifying the change in the blood of the mouse according to a method of detecting AA according to one aspect.

According to the composition and kit for the diagnosis of the level of senescence and the method of diagnosing senescence according to embodiments, the levels of senescence and anti-senescence can be easily diagnosed, the health condition of the subject is monitored, and a senescence-associated disease may be prevented or diagnosed.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A method of diagnosing a level of senescence of a subject, the method comprising:
   forming a complex by contacting a sample separated from the subject with an antibody specifically binding to arachidonic acid (AA) and arachidonic acid conjugated with enzymes;
   measuring an expression level of arachidonic acid in the sample by measuring a level of the complex;
   comparing the measured expression level of the arachidonic acid in the sample with a control group; and
   in the case of changes in the expression level of the arachidonic acid in the sample as compared with the control group, determining whether the level of senescence of the subject is low or level of senescence of the subject is high,
   wherein the measuring of the expression level is performed by an integrated magneto-electrochemical sensor (iMES) assay, and
   wherein the antibody is bound to magnetic heads.

2. The method of claim 1, wherein measuring of the expression level is performed by detecting signals from the one or more enzymes.

3. The method of claim 1, wherein the enzymes are selected from horse radish peroxidase (HRP), alkaline phosphatase (ALP), β-D-galactosidase (β-Gal), or any combination thereof.

4. The method of claim 2, wherein the signals are electrical currents released from the enzyme.

5. A method of diagnosing senescence-associated disease of a subject, the method comprising:
   forming a complex by contacting a sample separated from the subject with an antibody specifically binding to arachidonic acid (AA) and arachidonic acid conjugated with enzymes;
   measuring an expression level of arachidonic acid in the sample by measuring a level of the complex;
   comparing the measured expression level of the arachidonic acid in the sample with a control group; and
   in the case of changes in the expression level of arachidonic acid in the sample as compared with the control group, determining whether the subject has senescence-associated disease or a high risk of occurrence of senescence-associated disease,
   wherein the measuring of the expression level is performed by an integrated magneto-electrochemical sensor (iMES) assay;
   wherein the antibody is bound to magnetic beads, and
   wherein the senescence-associated disease is a cognitive disorder.

6. The method of claim 5, wherein the cognitive disorder is Alzheimer's disease, Parkinson's disease, dementia, or a combination thereof.

7. A method of diagnosing and treating a high level of senescence of a subject, the method comprising:
   (a) forming a complex by contacting a sample separated from the subject with an antibody specifically binding to arachidonic acid (AA) and arachidonic acid, conjugated with enzymes;
   (b) measuring an expression level of arachidonic acid in the sample by measuring a level of the complex;
   (c) comparing the measured expression level of the arachidonic acid in the sample with a control group;
   (d) determining whether the subject as the high level of senescence in accordance with the result of the comparing (c), wherein a change in the expression level of the arachidonic acid in the sample relative to the control group, is indicative of low or high level of senescence; and
   (e) administering an effective amount of a senescence inhibitor to the subject with high level of senescence,
   wherein the measuring of the expression level is performed by an integrated magneto-electrochemical sensor (iMES) assay, and
   wherein the antibody is bound to magnetic heads.

8. A method of diagnosing and treating senescence-associated disease of a subject, the method comprising:
   (a) forming a complex by contacting a sample separated from the subject with an antibody specifically binding to arachidonic acid (AA) and arachidonic acid conjugated with enzymes;
   (b) measuring an expression level of arachidonic acid in the sample by measuring a level of the complex;
   (c) comparing the measured expression level of the arachidonic acid in the sample with a control group;
   (d) determining whether the subject has the senescence-associated disease in accordance with the result of the comparing (c), wherein a change in the expression level of the arachidonic acid in the sample relative to the control group, is indicative of senescence associated disease; and (e) administering an effective amount of a senescence-associated disease medicine Or prophylactic agent to the subject diagnosed with having senescence-associated disease or high risk of occurrence of senescence-associated disease, wherein the measuring of the expression level is performed by an integrated magneto-electrochemical sensor (iMES) assay, wherein the antibody is bound to magnetic beads, and wherein the senescence-associated disease is a cognitive disorder.

* * * * *